United States Patent [19]
Deneulenaere

[11] Patent Number: 6,045,591
[45] Date of Patent: Apr. 4, 2000

[54] PROCESS FOR THE TWO-STEP DIRECT DYEING OF KERATIN FIBRES USING BASIC DIRECT DYES

[75] Inventor: Christelle Deneulenaere, Le Vesinet, France

[73] Assignee: L'Oreal, Paris, France

[21] Appl. No.: 09/206,694

[22] Filed: Dec. 7, 1998

[30] Foreign Application Priority Data

Dec. 5, 1997 [FR] France .................................. 97 15413

[51] Int. Cl.$^7$ ........................................................ A61K 7/13
[52] U.S. Cl. .................... 8/426; 8/405; 8/431; 8/618; 8/654; 8/655; 8/657; 8/659; 8/103; 8/107; 8/111; 8/931; 8/524; 8/526
[58] Field of Search ................................ 8/405, 407, 426, 8/431, 618, 654–659, 103, 107, 111, 931, 524, 526

[56] References Cited

U.S. PATENT DOCUMENTS

| | | | |
|---|---|---|---|
| 3,497,493 | 2/1970 | Grossmann | 534/613 |
| 3,649,654 | 3/1972 | Keller et al. | 8/426 |
| 3,679,347 | 7/1972 | Brown | 8/428 |
| 3,824,074 | 7/1974 | Bugaut et al. | 8/426 |
| 3,824,075 | 7/1974 | Kalopissis et al. | 8/431 |
| 3,955,918 | 5/1976 | Lang | 8/426 |
| 3,985,499 | 10/1976 | Lang et al. | 8/426 |
| 4,025,301 | 5/1977 | Lang | 8/426 |
| 4,182,612 | 1/1980 | Sokol et al. | 8/426 |
| 4,824,768 | 4/1989 | Grollier | 8/426 |
| 5,688,291 | 11/1997 | Said et al. | 8/431 |
| 5,713,961 | 2/1998 | Caisey et al. | 8/103 |
| 5,725,600 | 3/1998 | Caisey et al. | 8/103 |

FOREIGN PATENT DOCUMENTS

| | | |
|---|---|---|
| 0 512 879 | 11/1992 | European Pat. Off. . |
| 0 685 180 | 12/1995 | European Pat. Off. . |
| 0 685 220 | 12/1995 | European Pat. Off. . |
| 0 714 954 | 6/1996 | European Pat. Off. . |
| 1 585 308 | 1/1970 | France . |
| 2 703 588 | 10/1994 | France . |
| 2 703 589 | 10/1994 | France . |
| 2 715 065 | 7/1995 | France . |
| 2 716 804 | 9/1995 | France . |
| 19713696 | 6/1998 | Germany . |
| 880798 | 10/1961 | United Kingdom . |
| WO 95/01772 | 1/1995 | WIPO . |
| WO 95/15144 | 6/1995 | WIPO . |

OTHER PUBLICATIONS

English Language Derwent Abstract of EP 0 512 879, Nov. 1992.
English Language Derwent Abstract of EP 0 685 180, Dec. 1995.
English Language Derwent Abstract of EP 0 685 220, Dec. 1995.
English Language Derwent Abstract of EP 0 714 954, Jun. 1996.
English Language Derwent Abstract of France 1 585 308, Jan. 1970.
English Language Derwent Abstract of FR 2 703 588, Oct. 1994.
English Language Derwent Abstract of FR 2 703 589, Oct. 1994.
English Language Derwent Abstract of FR 2 715 065, Jul. 1995.
English Language Derwent Abstract of FR 2 716 804, Sep. 1995.

*Primary Examiner*—Caroline D. Liott
*Attorney, Agent, or Firm*—Finnegan, Henderson, Farabow & Garrett & Dunner L.L.P.

[57] ABSTRACT

The invention relates to a process for the two-step direct dyeing of keratin fibres, comprising bleaching the keratin fibres; and applying to the keratin fibres a dye composition comprising at least one partially dissolved basic direct dye and an aqueous medium, wherein the dye composition is ready to use or results from mixing, at the time of use, at least one pulverulent composition (P) comprising at least one basic direct dye and an aqueous composition (A).

23 Claims, No Drawings

PROCESS FOR THE TWO-STEP DIRECT DYEING OF KERATIN FIBRES USING BASIC DIRECT DYES

The invention relates to a process for the two-stage direct dyeing of keratin fibres, in particular human keratin fibres such as the hair, characterized in that, in a first step, the keratin fibres are bleached, and, in a second step, a dye composition, containing, in an aqueous medium, at least one partially dissolved basic direct dye is then applied to the keratin fibres, the said dye composition being ready to use or resulting from the mixing, at the time of use, of at least one pulverulent composition (P) containing at least one basic direct dye and an aqueous composition (A).

It is well known to dye keratin fibres, and in particular human hair, with dye compositions containing direct dyes and in particular nitrobenzene direct dyes. However, when direct dyes are incorporated into dye compositions, they have the drawback of giving colourings which are not sufficiently fast, in particular with respect to shampooing. Furthermore, the colourings obtained generally lack intensity and are too dull.

In order to overcome this problem, it has already been proposed to bleach keratin fibres prior to any step of application of direct dyes. However, although the application of direct dyes to bleached keratin fibres leads to colourings which are less dull than those obtained without pre-bleaching the fibres, this nevertheless gives colourings which are not sufficiently chromatic or intense and are non-uniform, i.e. they show local differences in intensity.

It is in seeking to overcome these problems that the Inventor has now discovered, surprisingly, that it is possible to obtain intense, very chromatic and uniform colourings which also have good resistance with respect to atmospheric agents such as light and bad weather, and with respect to perspiration and the various treatments to which the hair may be subjected (washing, permanent-waving), by carrying out a process of two-stage direct dyeing of keratin fibres which involves, in a first step, bleaching the keratin fibres, and, in a second step, applying to these fibres a dye composition containing, in an aqueous medium, at least one partially dissolved basic direct dye, the said dye composition being ready to use or resulting from the mixing, at the time of use, of at least one pulverulent composition (P) containing at least one basic direct dye and an aqueous composition (A).

The dyeing process in accordance with the invention can also dye the keratin fibres in short dye-application times.

This discovery forms the basis for the present invention.

The subject of the present invention is thus a process for the two-step direct dyeing of keratin fibres, by first bleaching the keratin fibres and then applying to the keratin fibres a dye composition including at least one partially dissolved basic direct dye and an aqueous medium, wherein the dye composition is ready to use or results from mixing, at the time of use, at least one pulverulent composition comprising at least one basic direct dye and an aqueous composition.

According to the invention, the fact that the basic direct dye(s) present in the dye composition applied during the second step of the process in accordance with the invention is (are) partially dissolved either means that the basic direct dye(s) is (are) in supersaturation, i.e. they have an amount by weight which is greater than their solubility limit in the aqueous dyeing medium used, or means that the basic direct dye(s) is (are) partially or totally adsorbed onto or coated with an insoluble inorganic or organic filler present in the dye composition.

According to the invention, the first step of the process in accordance with the invention is a bleaching step which leads to a shade (after bleaching) preferably having a tone height of greater than or equal to 6.

In the keratin fibre dyeing sector, the colour of the keratin fibres can be expressed in tone heights ranging from 1 to 10 and corresponding to the following shades:

| Tone height | Corresponding shade |
|---|---|
| 10 | Extremely light blonde |
| 9 | Very light blonde |
| 8 | Light blonde |
| 7 | Blonde |
| 6 | Dark blonde |
| 5 | Light chestnut |
| 4 | Chestnut |
| 3 | Dark chestnut |
| 2 | Brown |
| 1 | Black |

Preferably, the bleaching step leads to a shade which shows a colour difference of greater than or equal to 2 tones when compared with the colour of the fibres before bleaching. The results are proportionately better the closer the tone heights are, after the bleaching step, to values of 9 or 10.

Any type of method for bleaching keratin fibres can be used according to the process of the invention.

According to a first embodiment of the process of the invention, the bleaching can be carried out by applying an oxidizing composition containing at least one oxidizing agent.

The time required to obtain the desired bleaching is generally between 15 and 60 minutes and even more particularly between 30 and 45 minutes.

The nature of the oxidizing agent present in the oxidizing composition is not critical. Among these oxidizing agents, mention may be made in particular of hydrogen peroxide, urea peroxide, alkali metal bromates, persalts such as perborates, persulphates and percarbonates, and polythionates, and mixtures thereof.

The oxidizing composition can be in liquid or creamy form, the said oxidizing composition being ready to use or resulting from the mixing, at the time of use, of one or more aqueous compositions or of one or more aqueous compositions with one or more pulverulent compositions, the oxidizing agent being present in the aqueous composition(s) and/or in the pulverulent composition(s).

When the oxidizing agent is present in the pulverulent composition, this composition can then be in granular or coated form, as is described, for example, in patent applications FR-A-2,703,588, FR-A-2,703,589, FR-A-2,715,065 and FR-A-2,716,804, the entire contents of which are incorporated herein by reference.

The pH of the oxidizing composition is preferably between 5 and 12 and even more particularly between 8 and 11, and it can be adjusted to the desired value using acidifying or basifying agents which are well known in the state of the art in the bleaching of keratin fibres.

Among the basifying agents, mention may be made, for example, of aqueous ammonia, alkali metal carbonates, alkanolamines such as mono-, di- and triethanolamine and derivatives thereof, sodium hydroxide, potassium hydroxide or the compounds described in patent application EP-A-512,879, the entire contents of which are incorporated herein by reference, and among which mention may be made in particular of 1,3-diaminopropane, N,N'-diethyl-1,3-diaminopropane, N,N-diethyl-1,3-diaminopropane, N,N- dimethyl-1,3-diaminopropane, 2-hydroxy-1-(N,N-diethyl) amino-3-aminopropane and 2-hydroxy-1,3-diaminopropane.

The acidifying agents are conventionally, for example, inorganic or organic acids such as hydrochloric acid, orthophosphoric acid, carboxylic acids such as tartaric acid, citric acid or lactic acid, or sulphonic acids.

The oxidizing composition used according to the process in accordance with the invention can also contain one or more adjuvants used conventionally in compositions for bleaching keratin fibres, such as surfactants, polymers, inorganic or organic thickeners, antioxidants, penetrating agents, sequestering agents, fragrances, buffers, dispersing agents, conditioners, film-forming agents, ceramides, preserving agents and opacifiers.

When the bleaching step using the oxidizing composition is complete, the keratin fibres are preferably rinsed with water before the second step of applying the dye composition containing the partially dissolved basic direct dye(s). The rinsing can also be followed by shampooing in order to remove any traces of oxidizing agent.

According to a second embodiment of the process of the invention, the bleaching step can be carried out by irradiating the keratin fibres with laser light in the form of pulses which are powerful enough to degrade the melanin contained in the keratin fibres and thus lead to the bleaching.

This method of bleaching by laser irradiation is described in the patent applications EP-A-685,220 and EP-A-685,180, the entire contents of which are incorporated herein by reference.

The basic direct dye(s) which can be used in the dye composition used during the second step of the process in accordance with the invention is (are) preferably chosen from basic aminoanthraquinone dyes, basic mono- or diazo dyes, basic azomethine dyes, basic naphthoquinone dyes and basic dyes containing ethylenic monounsaturations.

As examples, mention may be made in particular of [8-[(p-aminophenyl)azo]-7-hydroxy-2-naphthyl] trimethylammonium chloride (also known as Basic Brown 16 or Arianor Mahogany 306002 in the Color Index), the combination of 3-[(4-amino-6-bromo-5,8-dihydro-1 -hydroxy-8-imino-5-oxo-2-naphthyl)amino]-N,N,N-trimethylbenzenaminium chloride and of 3-[(2,6-dibromo-5,8-dihydro-1-hydroxy-8-imino-5-oxo-3-naphthyl)amino]-N,N,N-trimethylbenzenaminium chloride (also known as Basic Blue 99 or Arianor Steel Blue 306004 in the Color Index), 7-hydroxy-8-[(2-methoxyphenyl)azo]-N,N,N-trimethyl- 2-naphthalenaminium chloride (also known as Basic Red 76 or Arianor Madder Red in the Color Index), [8-[(4-amino-2-nitrophenyl)azo]-7-hydroxy-2-naphthyl] trimethylammonium chloride (also known as Basic Red 118 in the Color Index), the combination of [8-[(4-amino-3-nitrophenyl)azo]-7-hydroxy-2-naphthyl] trimethylammonium chloride and of [8-[(4-amino-2-nitrophenyl)azo]-7-hydroxy-2-naphthyl] trimethylammonium chloride (also known as Brown 17 or Arianor Sienna Brown 306001 in the Color Index), 3-[(4,5-dihydro-3-methyl-5-oxo-1-phenyl-1H-pyrazol-4-yl)azo]-N,N,N-trimethylbenzenaminium chloride (also known as Basic Yellow 57 or Arianor Straw Yellow 306005 in the Color Index), 1-(γ-aminopropyl)aminoanthraquinone hydrochloride, 1-N-(methylmorpholiniumpropyl)amino-4-hydroxyanthraquinone methyl sulphate and Basic Orange 69 (Color Index name), and Basic Red 51 (also known as Basacryl Red X-BL and Maxilon Red M-RL).

The basic direct dye(s) can also be chosen from:

a) a compound of formula (I):

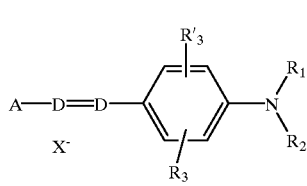

(I)

wherein:

D represents a nitrogen atom or a —CH group;

$R_1$ and $R_2$, which may be identical or different, represent a hydrogen atom; a $C_1$–$C_4$ alkyl radical which can be substituted with a —CN, —OH or —NH$_2$ radical or form, with a carbon atom of the benzene ring, a heterocycle optionally containing oxygen or an additional nitrogen or both, which can be substituted with one or more $C_1$–$C_4$ alkyl radicals; or a 4'-aminophenyl radical;

$R_3$ and $R'_3$, which may be identical or different, represent a hydrogen atom or a halogen atom, or a cyano, $C_1$–$C_4$ alkoxy or acetyloxy radical;

$X^-$ represents an anion; and

A represents:

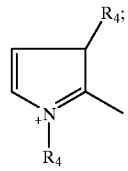

A$_1$

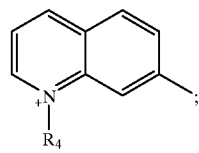

A$_2$

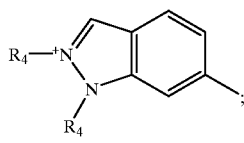

A$_3$

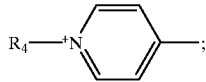

A$_4$

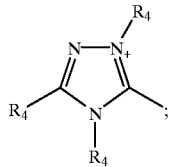

A$_5$

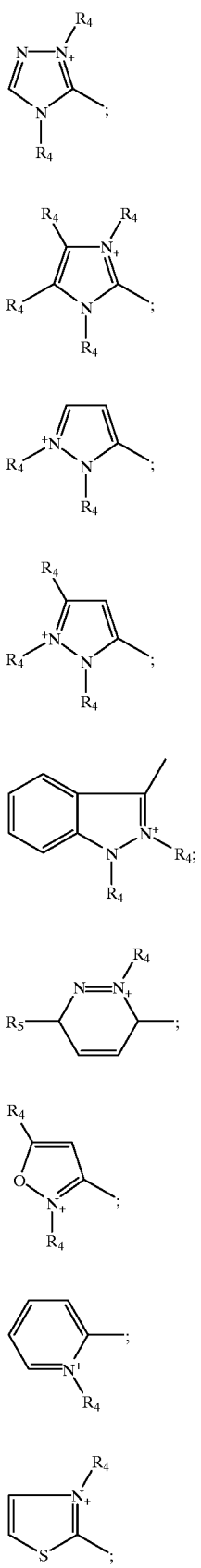

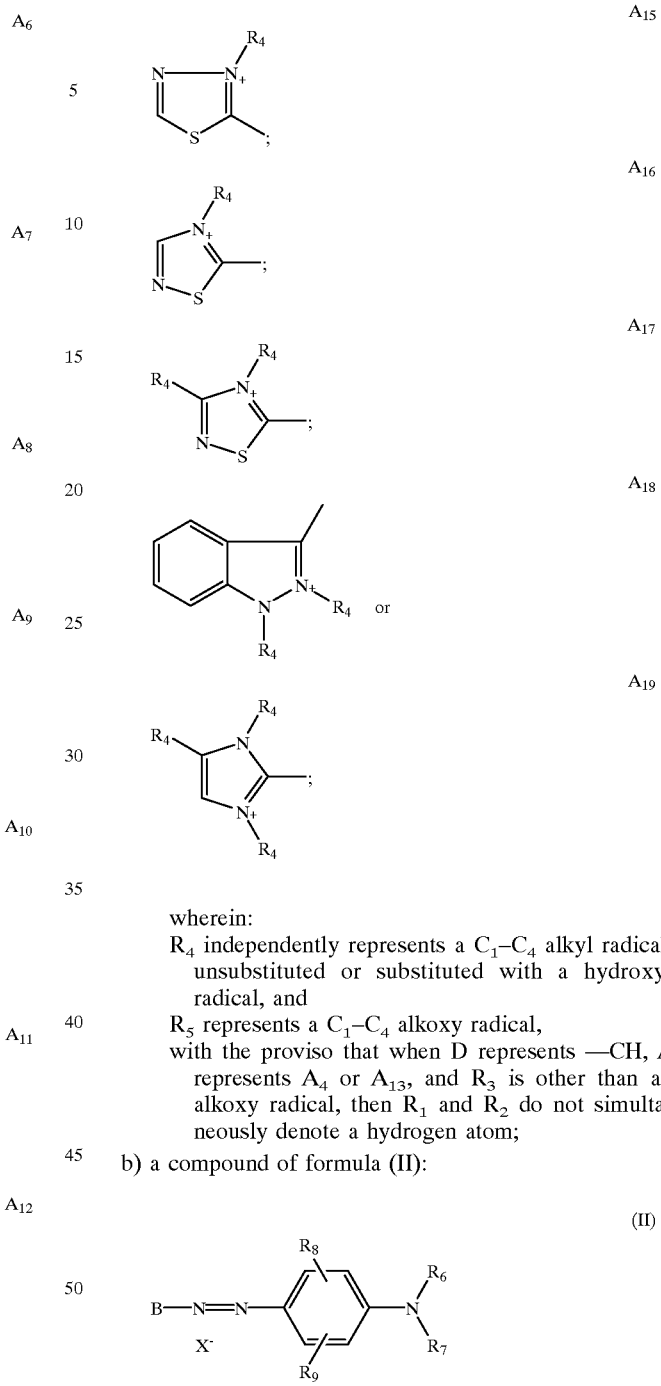

wherein:
$R_4$ independently represents a $C_1$–$C_4$ alkyl radical, unsubstituted or substituted with a hydroxyl radical, and
$R_5$ represents a $C_1$–$C_4$ alkoxy radical,
with the proviso that when D represents —CH, A represents $A_4$ or $A_{13}$, and $R_3$ is other than an alkoxy radical, then $R_1$ and $R_2$ do not simultaneously denote a hydrogen atom;

b) a compound of formula (II):

wherein:
$R_6$ represents a hydrogen atom or a $C_1$–$C_4$ alkyl radical;
$R_7$ represents a hydrogen atom, an alkyl radical which can be substituted with a —CN radical or with an amino group, or a 4'-aminophenyl radical, or forms with $R_6$ a heterocycle containing oxygen or an additional nitrogen or both, unsubstituted or substituted with a $C_1$–$C_4$ alkyl radical;
$R_8$ and $R_9$, which may be identical or different, represent a hydrogen atom, a halogen atom, a $C_1$–$C_4$ alkyl, $C_1$–$C_4$ alkoxy, or a —CN radical;

$X^-$ represents an anion; and
B represents:

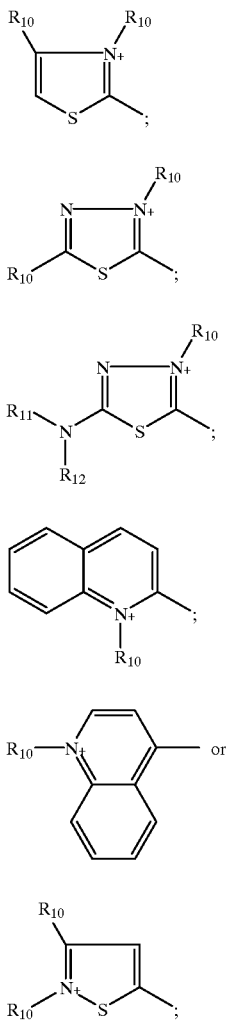

wherein:
$R_{10}$ independently represents a $C_1$–$C_4$ alkyl radical, and $R_{11}$ and $R_{12}$, which may be identical or different, represent a hydrogen atom or a $C_1$–$C_4$ alkyl radical;

c) a compound of formulae (III) or (III'):

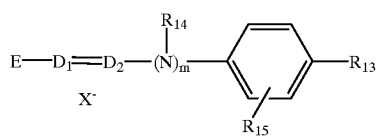
(III)

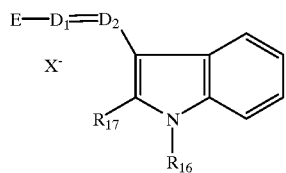
(III')

wherein:
$R_{13}$ represents a hydrogen atom, a $C_1$–$C_4$ alkoxy radical, a halogen atom or an amino radical;
$R_{14}$ represents a hydrogen atom, a $C_1$–$C_4$ alkyl radical or forms, with a carbon atom of the benzene ring, a heterocycle, wherein said heterocycle optionally contains oxygen, and is unsubstituted or substituted with one or more $C_1$–$C_4$ alkyl groups;
$R_{15}$ represents a hydrogen atom or a halogen atom;
$R_{16}$ and $R_{17}$, which may be identical or different, represent a hydrogen atom or a $C_1$–$C_4$ alkyl radical;
$D_1$ and $D_2$, which may be identical or different, represent a nitrogen atom or a —CH group;
m represents 0 or 1;
wherein when $R_{13}$ represents an unsubstituted amino group, then $D_1$ and $D_2$ simultaneously represent a —CH group and m=0;
$X^-$ represents an anion; and
E represents a group chosen from the structures E1 to E8 below:

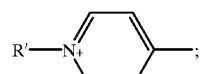
E1

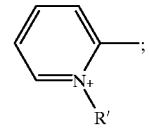
E2

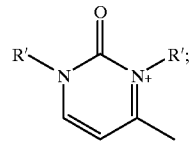
E3

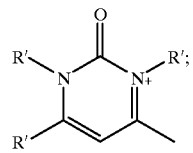
E4

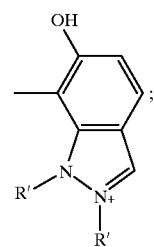
E5

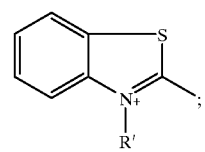
E6

-continued

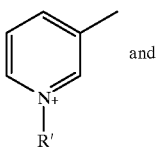
E7 and

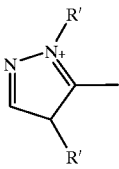
E8 wherein R' represents a $C_1$–$C_4$ alkyl radical;
wherein when m=0 and $D_1$ represents a nitrogen atom, then E may also represent:

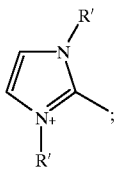
E9 wherein R' represents a $C_1$–$C_4$ alkyl radical; or the basic direct dye is
d) a compound of formula (IV):

$$G-N=N-J \quad (IV)$$

wherein:
G represents $G_1$, $G_2$ or $G_3$:

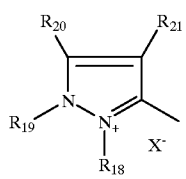
$G_1$

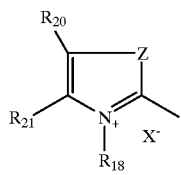
$G_2$

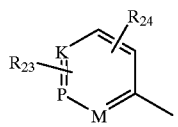
$G_3$ wherein:
$R_{18}$ denotes a $C_1$–$C_4$ alkyl radical, a phenyl radical, unsubstituted or substituted with a $C_1$–$C_4$ alkyl radical or a halogen atom;
$R_{19}$ denotes a $C_1$–$C_4$ alkyl radical or a phenyl radical;

$R_{20}$ and $R_{21}$, which may be identical or different, represent a $C_1$–$C_4$ alkyl radical, a phenyl radical, or
$R_{20}$ and $R_{21}$ together form, in $G_1$, a benzene ring substituted with one or more $C_1$–$C_4$ alkyl, $C_1$–$C_4$ alkoxy or $NO_2$ radicals, or
$R_{20}$ and $R_{21}$ together form, in $G_2$, a benzene ring unsubstituted or substituted with one or more $C_1$–$C_4$ alkyl, $C_1$–$C_4$ alkoxy or $NO_2$ radicals;
$R_{20}$ may also denote a hydrogen atom;
Z denotes an oxygen or sulphur atom or a group —$NR_{19}$;
M represents a —CH, —CR or —$NR_{22}(X^-)_r$ group, wherein R denotes $C_1$–$C_4$ alkyl and r denotes zero or 1;
K represents a —CH, —CR or —$NR_{22}(X^-)_r$ group, wherein R denotes $C_1$–$C_4$ alkyl and r denotes zero or 1;
P represents a —CH, —CR or —$NR_{22}(X^-)_r$ group, wherein R denotes $C_1$–$C_4$ alkyl and r denotes zero or 1;
$R_{22}$ represents an atom $O^-$, a $C_1$–$C_4$ alkoxy radical or a $C_1$–$C_4$ alkyl radical; $R_{23}$ and $R_{24}$, which may be identical or different, represent a hydrogen atom, a halogen atom, a $C_1$–$C_4$ alkyl or $C_1$–$C_4$ alkoxy radical or an —$NO_2$ radical;
$X^-$ represents an anion;
with the provisos that,
if $R_{22}$ denotes $O^-$, then r denotes zero;
if K or P or M denotes —N—$(C_1$–$C_4)$alkyl $X^-$, then $R_{23}$ or $R_{24}$ is other than a hydrogen atom;
if K denotes —$NR_{22}(X^-)_r$, then M=P=—CH or —CR;
if M denotes —$NR_{22}(X^-)_r$, then K=P=—CH or —CR;
if P denotes —$NR_{22}(X^-)_r$, then K=M=—CH or —CR;
if Z denotes a sulphur atom with $R_{21}$ denoting $C_1$–$C_4$ alkyl, then $R_{20}$ is other than a hydrogen atom; and
if Z denotes —$NR_{22}$ with $R_{19}$ denoting $C_1$–$C_4$ alkyl, then at least one of the
radicals $R_{18}$, $R_{20}$ or $R_{21}$ of $G_2$ is other than a $C_1$–$C_4$ alkyl radical;
J represents:
(i) a group of structure $J_1$:

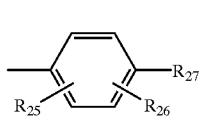
$J_1$ wherein:
$R_{25}$ represents a hydrogen atom, a halogen atom, a $C_1$–$C_4$ alkyl or $C_1$–$C_4$ alkoxy radical, a radical —OH, —$NO_2$, —$NHR_{28}$, —$NR_{29}R_{30}$, or —$NHCO(C_1$–$C_4)$alkyl, or forms, with $R_{26}$, a 5- or 6-membered ring which may or may not contain one or more hetero atoms chosen from nitrogen, oxygen and sulphur;
$R_{26}$ represents a hydrogen atom, a halogen atom, a $C_1$–$C_4$ alkyl or $C_1$–$C_4$ alkoxy radical, or forms, with $R_{27}$ or $R_{28}$, a 5- or 6-membered ring which may or may not contain one or more hetero atoms chosen from nitrogen, oxygen and sulphur;
$R_{27}$ represents a hydrogen atom, an —OH radical, an —$NHR_{28}$ radical or an —$NR_{29}R_{30}$ radical;

$R_{28}$ represents a hydrogen atom, a $C_1$–$C_4$ alkyl radical, a $C_1$–$C_4$ monohydroxyalkyl radical, a $C_2$–$C_4$ polyhydroxyalkyl radical or a phenyl radical;

$R_{29}$ and $R_{30}$, which may be identical or different, represent a $C_1$–$C_4$ alkyl radical, a $C_1$–$C_4$ monohydroxyalkyl radical or a $C_2$–$C_4$ polyhydroxyalkyl radical;

(ii) a 5- or 6-membered heterocyclic group containing nitrogen, which can contain other hetero atoms or carbonyl groups and can be substituted with one or more $C_1$–$C_4$ alkyl, amino or phenyl radicals, or a group of structure $J_2$:

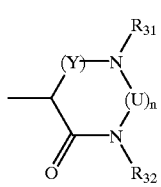

wherein:
$R_{31}$ and $R_{32}$, which may be identical or different, represent a hydrogen atom, a $C_1$–$C_4$ alkyl radical or a phenyl radical;

Y denotes a —CO— radical or a radical

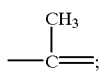

and
n=0 or 1, wherein when n is 1, U denotes a —CO— radical.

In the structures (I) to (IV) defined above, the $C_1$–$C_4$ alkyl or alkoxy group preferably denotes methyl, ethyl, butyl, methoxy or ethoxy.

The basic direct dyes of formulae (I), (II), (III) and (III') which can be used in the dye composition used during the second step of the process in accordance with the invention are known compounds and are described, for example, in the patent applications WO 95101772, WO 95/15144 and EP-A-0,714,954, the entire contents of which are incorporated herein by reference.

Among the basic direct dyes of formula (I), mention may be made more particularly of the cationic compounds corresponding to structures (I1) to (I52) below:

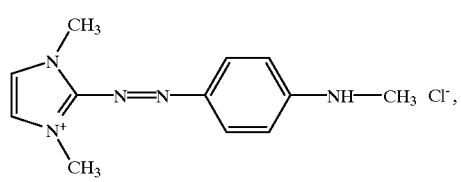
(I1)

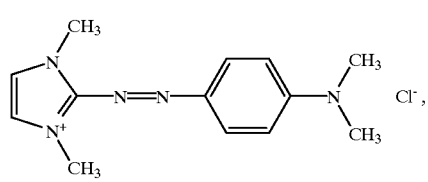
(I2)

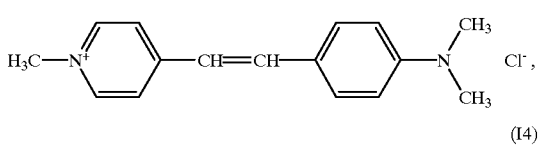
(I3)

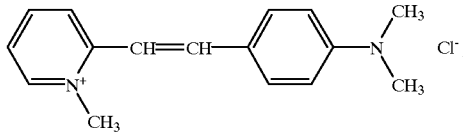
(I4)

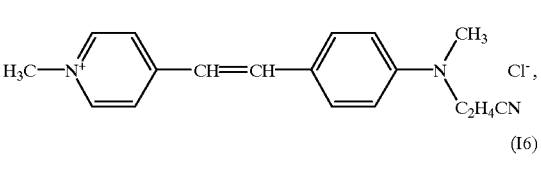
(I5)

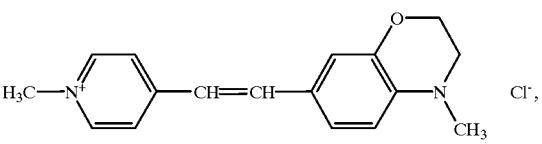
(I6)

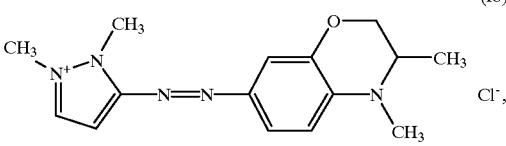
(I7)

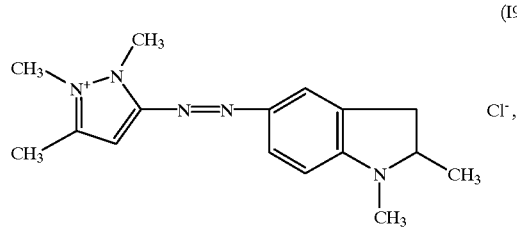
(I8)

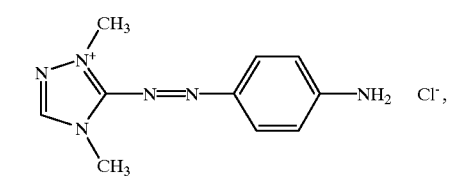
(I9)

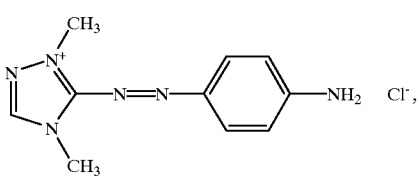
(I10)

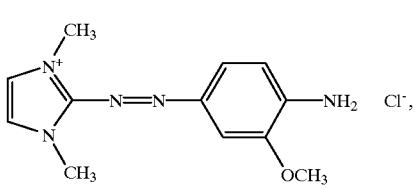
(I11)

-continued
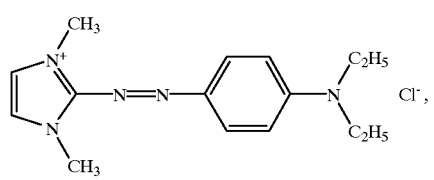 (I12)
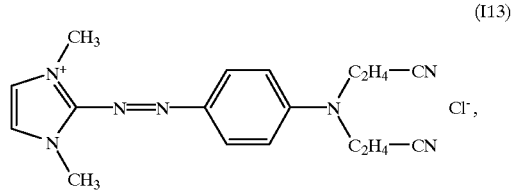 (I13)
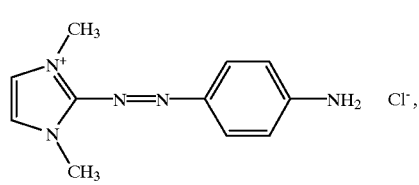 (I14)
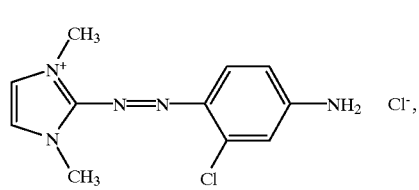 (I15)
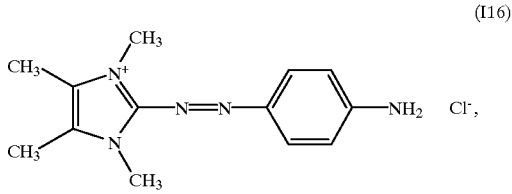 (I16)
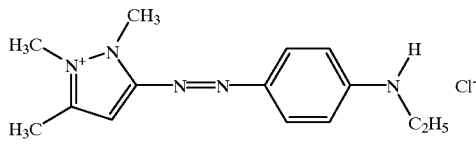 (I17)
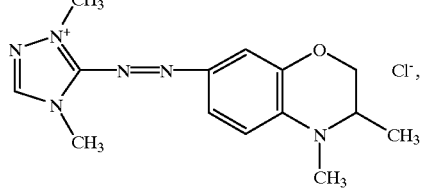 (I18)
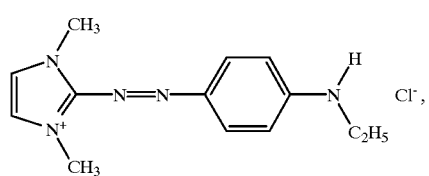 (I19)
-continued
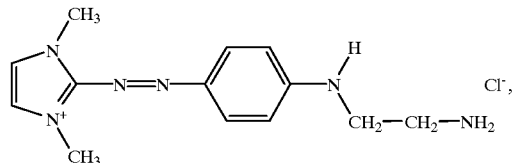 (I20)
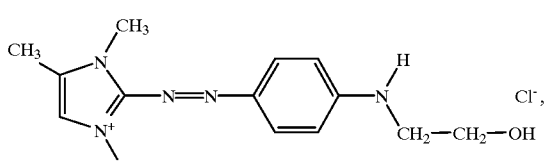 (I21)
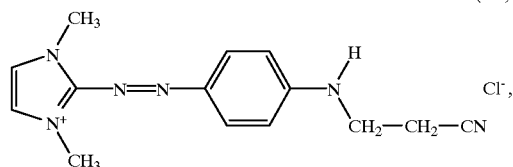 (I22)
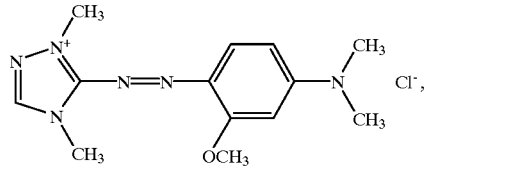 (I23)
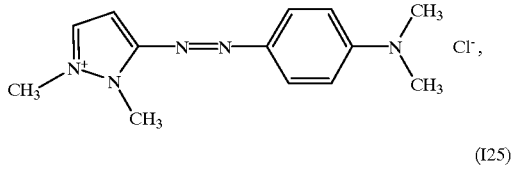 (I24)
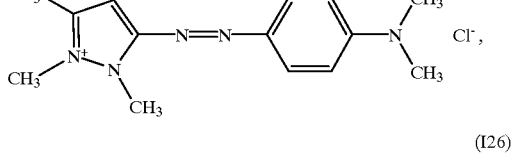 (I25)
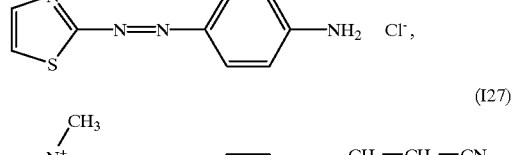 (I26)
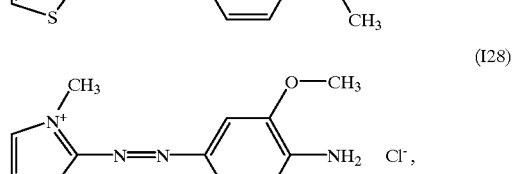 (I27)
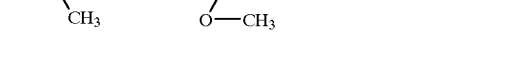 (I28)

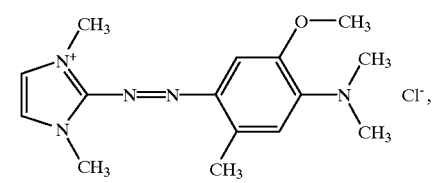 (I29)
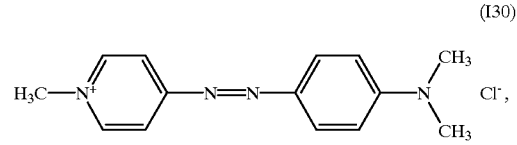 (I30)
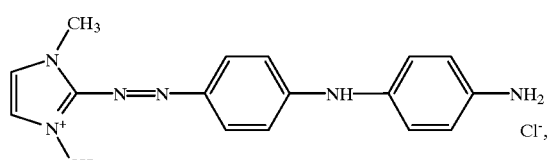 (I31)
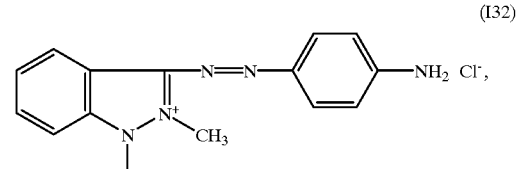 (I32)
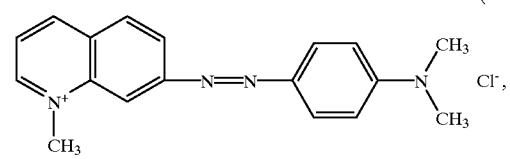 (I33)
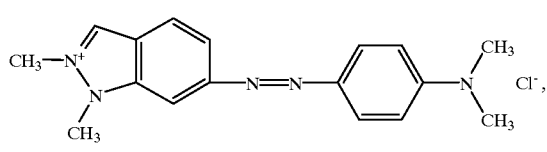 (I34)
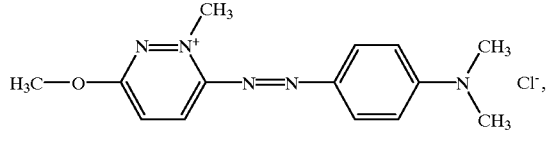 (I35)
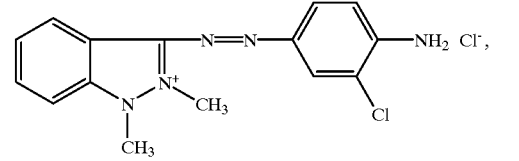 (I36)
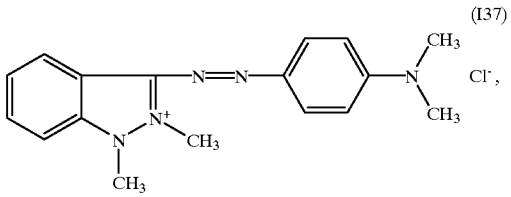 (I37)
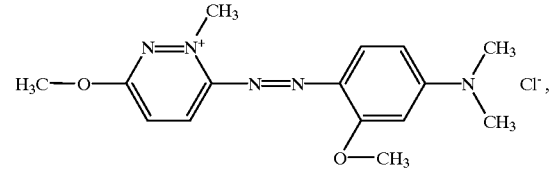 (I38)
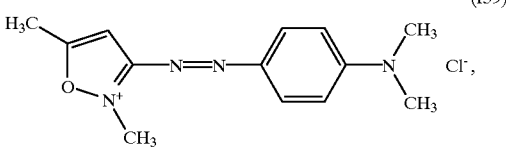 (I39)
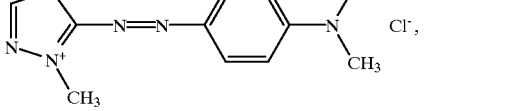 (I40)
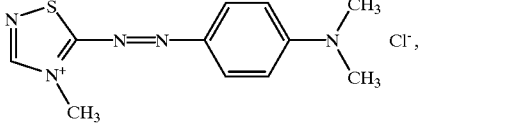 (I41)
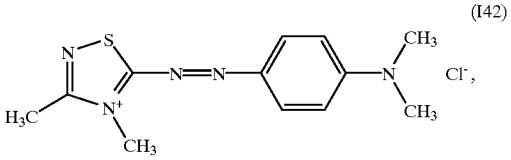 (I42)
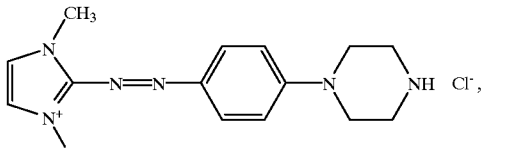 (I43)
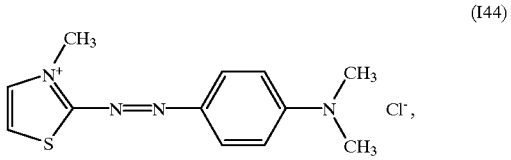 (I44)
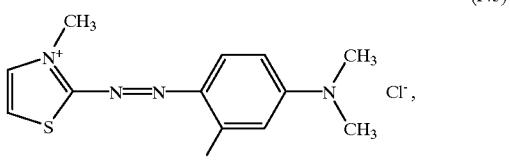 (I45)

(I46) 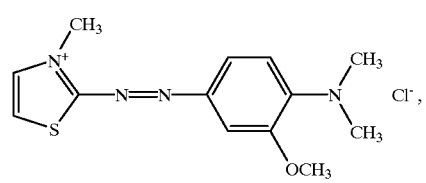
(I47) 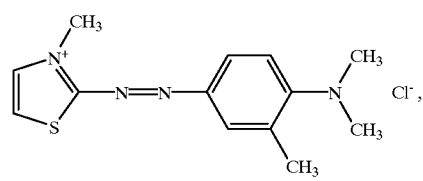
(I48) 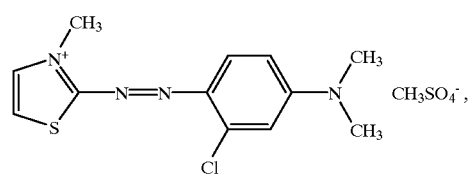
(I49) 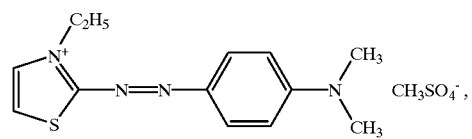
(I50) 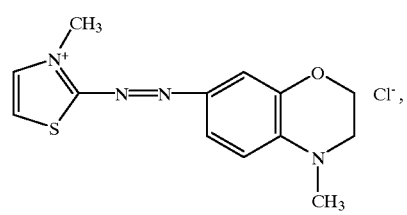
(I51) 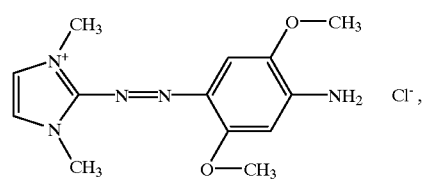
and
(I52) 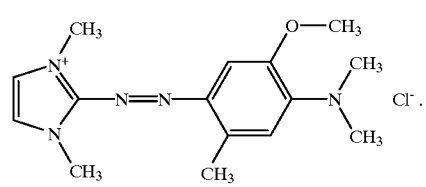
Among the compounds of structures (I1) to (I52) described above, the compounds most particularly preferred are those corresponding to the structures (I1), (I2), (I14) and (I31).
Among the basic direct dyes of formula (II), mention may be made more particularly of the compounds corresponding to the structures (II1) to (II12) below:
(II1) 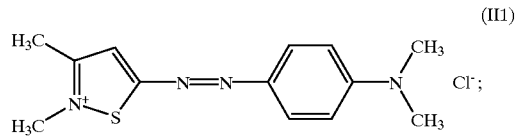
(II2) 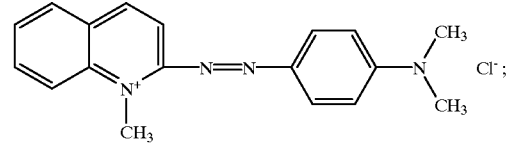
(II3) 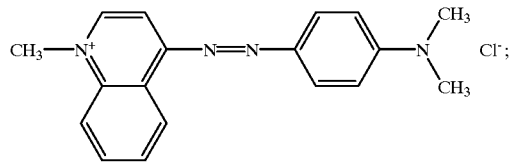
(II4) 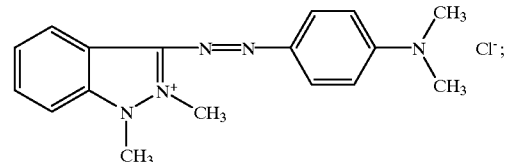
(II5) 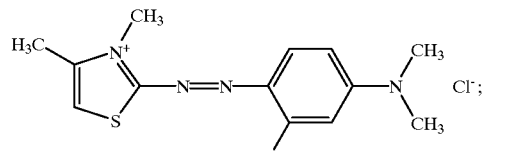
(II6) 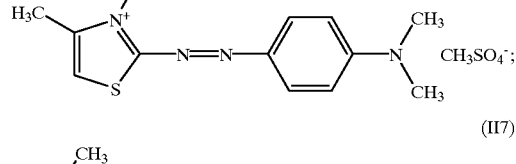
(II7) 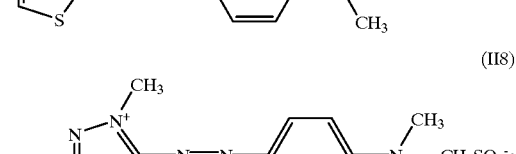
(II8) 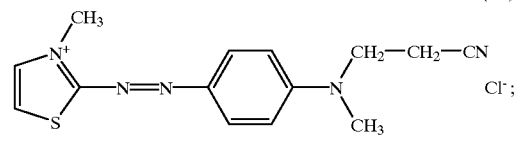
(II9)

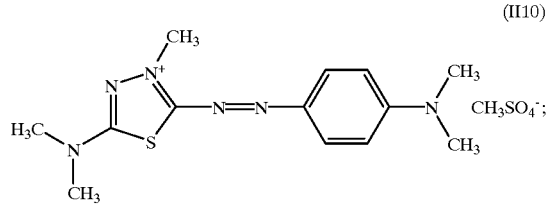
(II10)
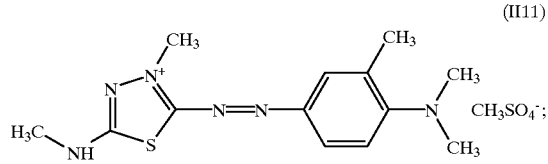
(II11)
et
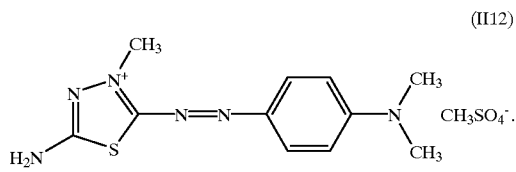
(II12)
Among the basic direct dyes of formula (III), mention may be made more particularly of the compounds corresponding to the structures (III1) to (III18) below:
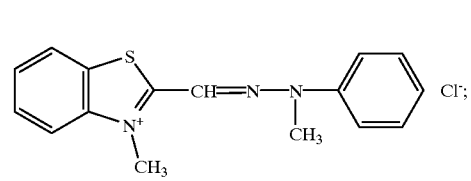
(III1)
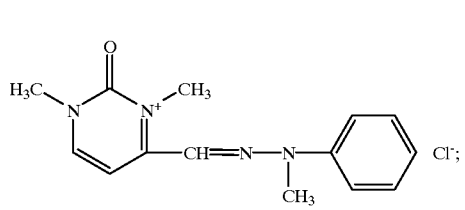
(III2)
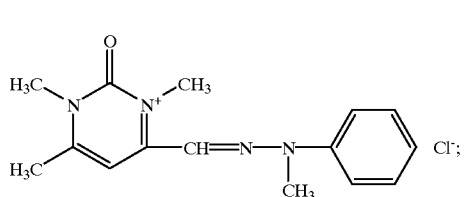
(III3)
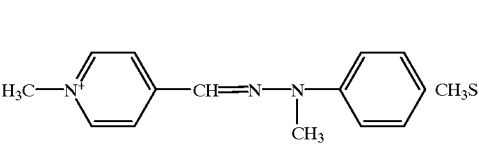
(III4)
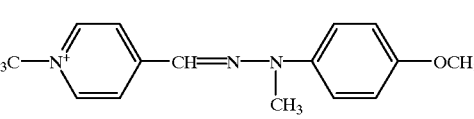
(III5)
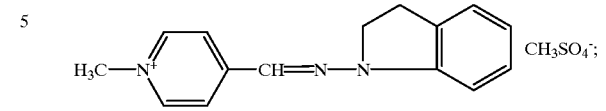
(III6)
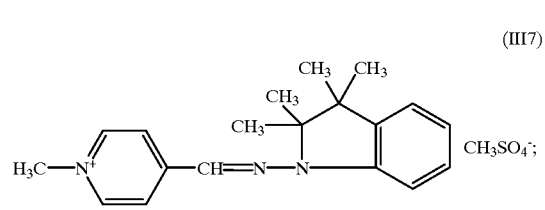
(III7)
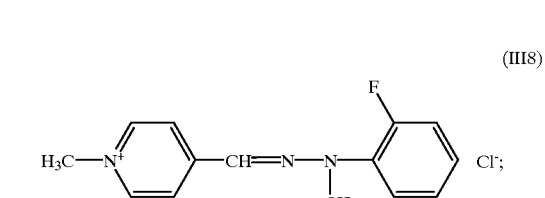
(III8)
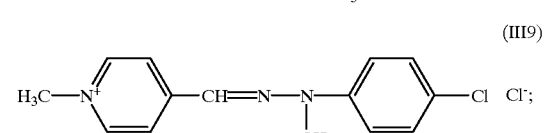
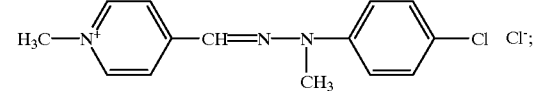
(III9)
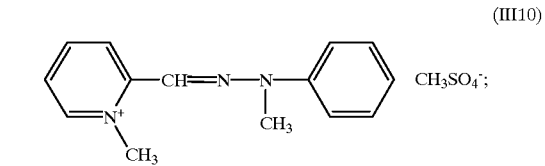
(III10)
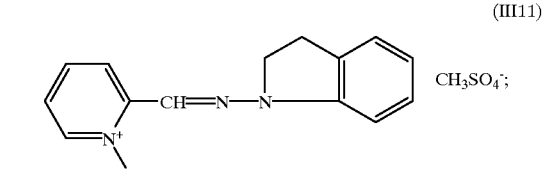
(III11)
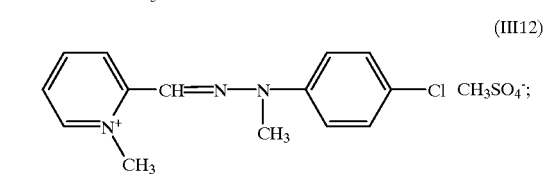
(III12)
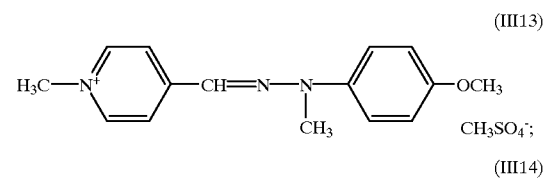
(III13)
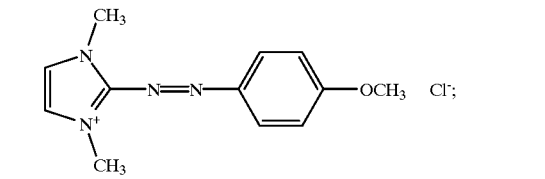
(III14)

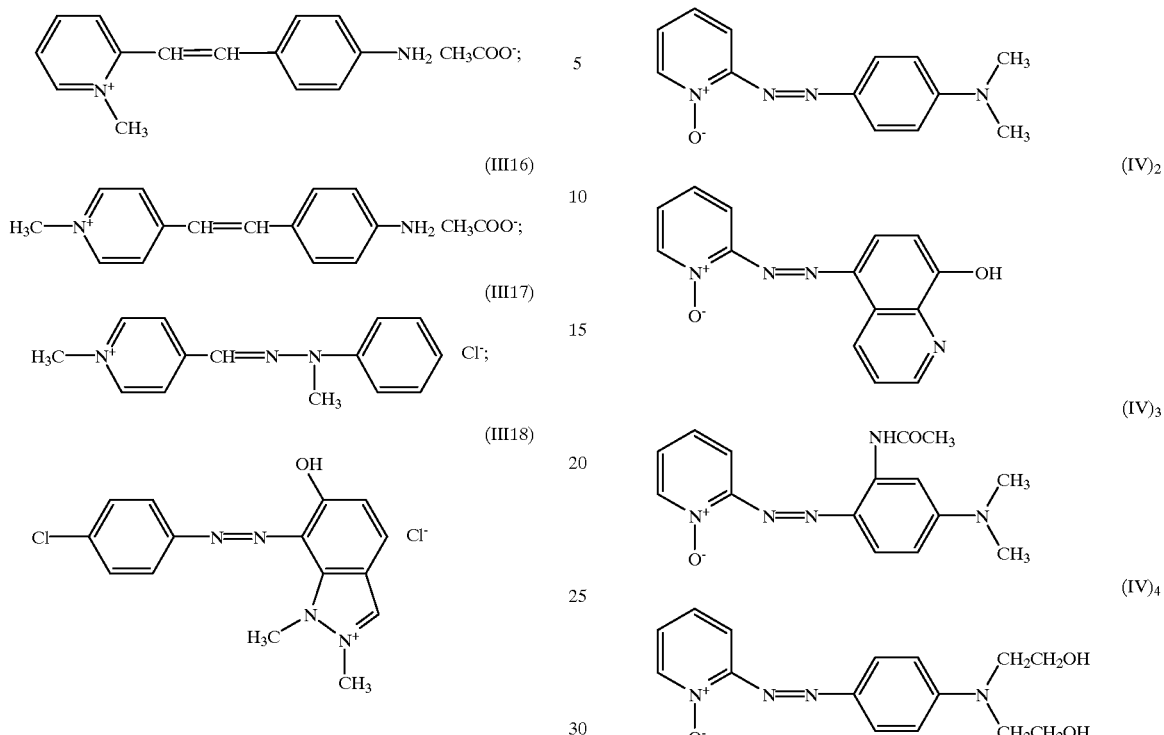

Among the specific compounds of the structures (III1) to (III18) described above, the compounds most particularly preferred are those corresponding to the structures (III4), (III5) and (III13).

Among the basic direct dyes of formula (III'), mention may be made more particularly of the compounds corresponding to the structures (III'1) to (III'3) below:

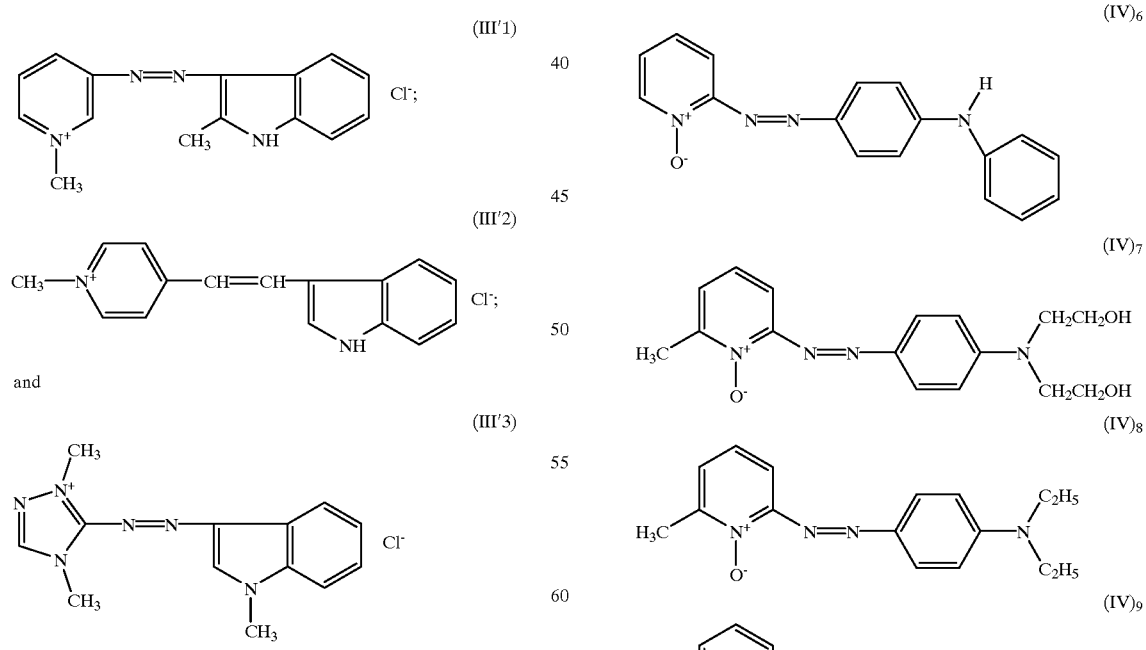

Among the cationic basic direct dyes of formula (IV) which can be used in the dye compositions in accordance with the invention, mention may be made more particularly of the compounds of structures $(IV)_1$ to $(IV)_{77}$ below:

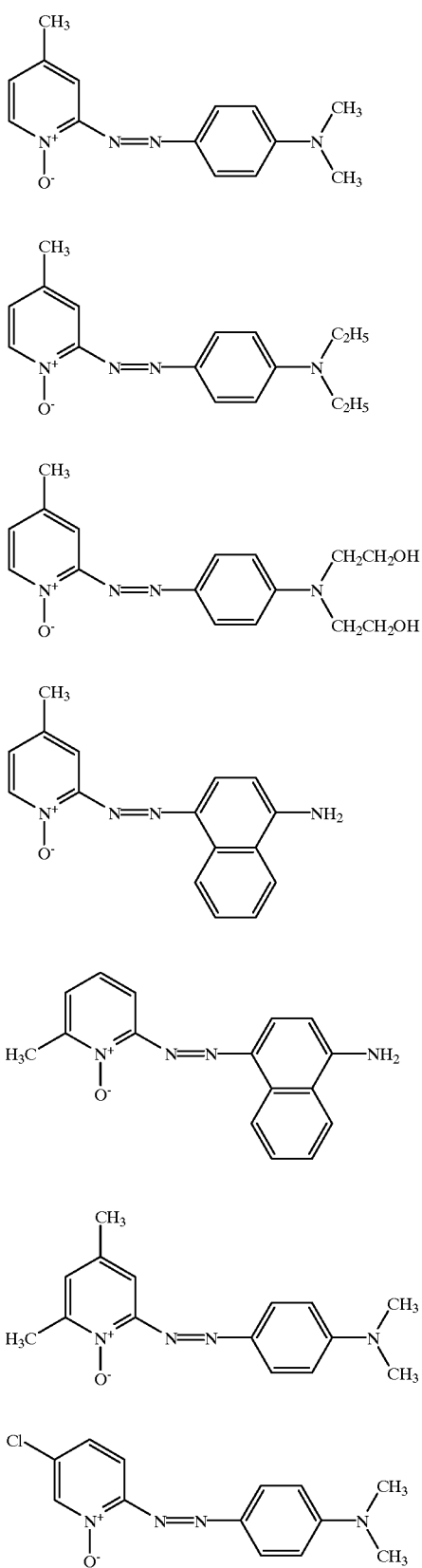
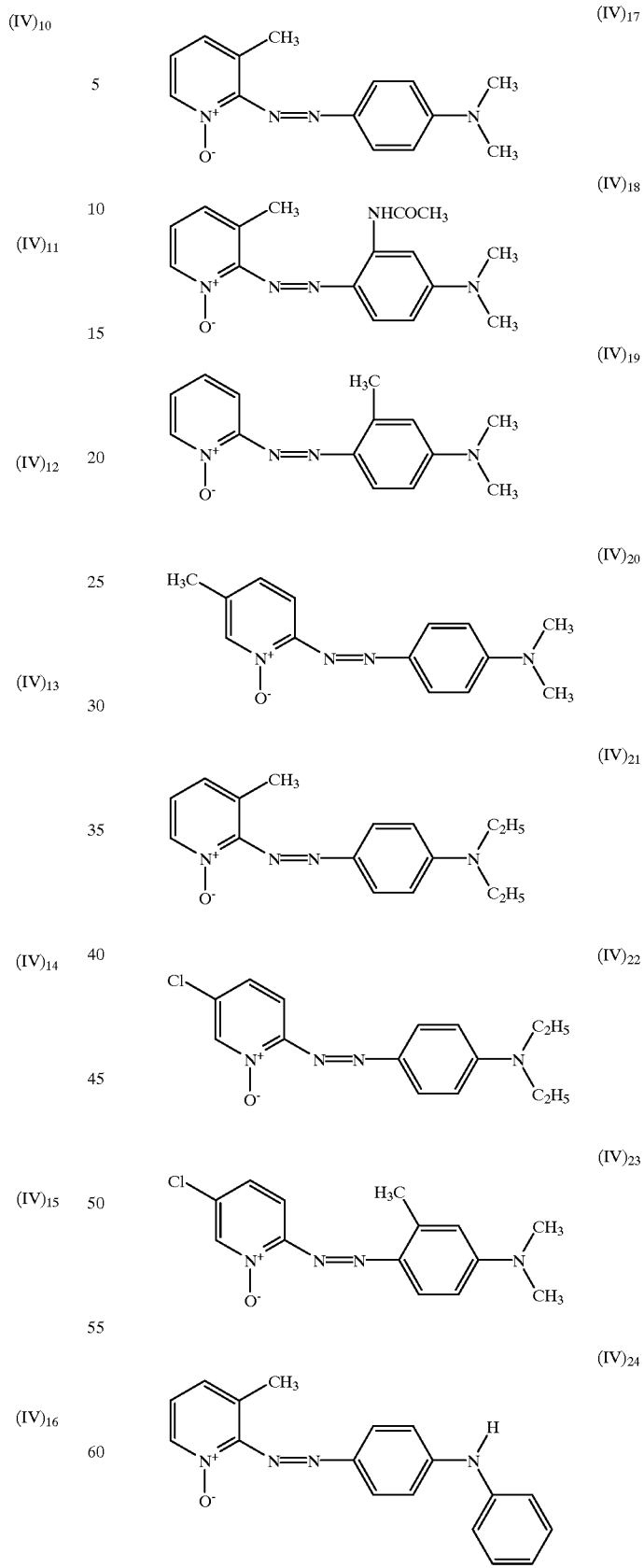

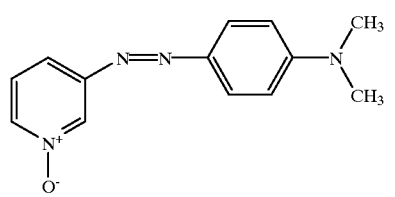
(IV)25
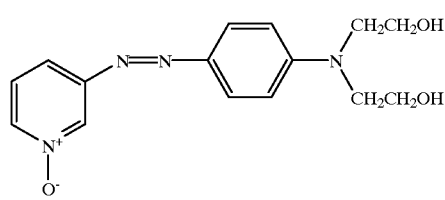
(IV)26
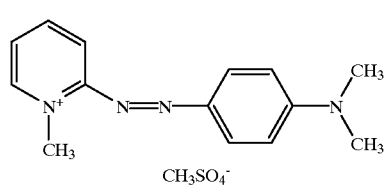
(IV)27
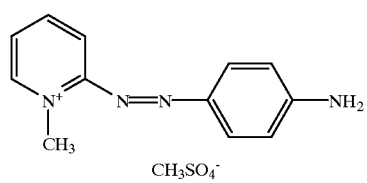
(IV)28
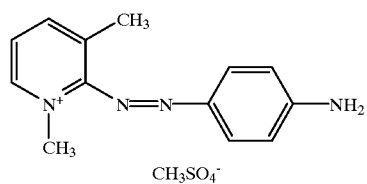
(IV)29
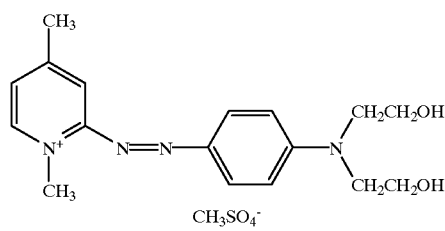
(IV)30
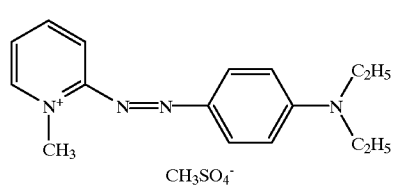
(IV)31
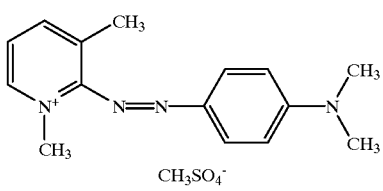
(IV)32
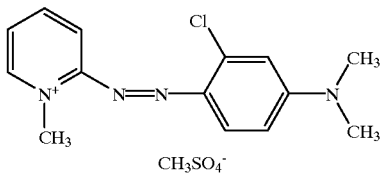
(IV)33
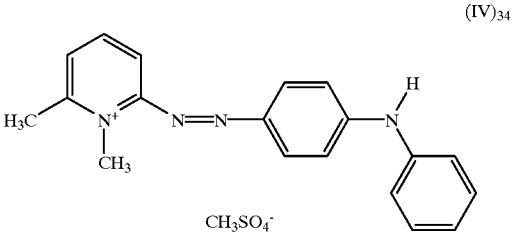
(IV)34
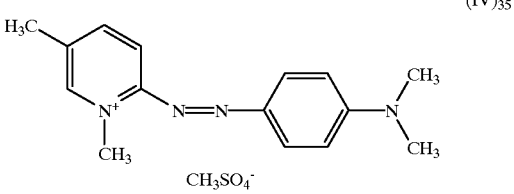
(IV)35
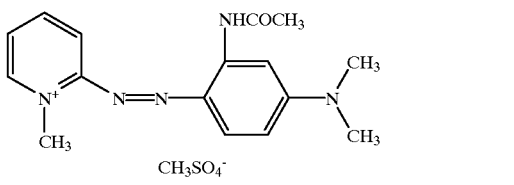
(IV)36
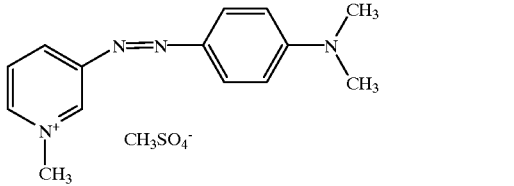
(IV)37
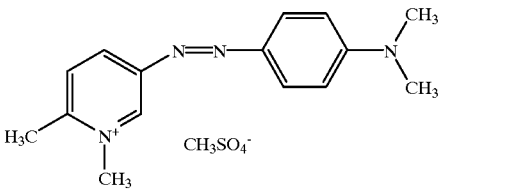
(IV)38

-continued
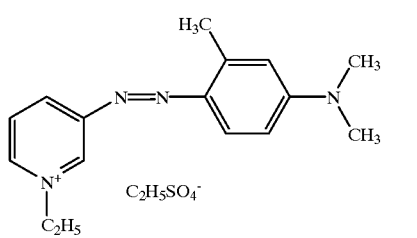
(IV)39
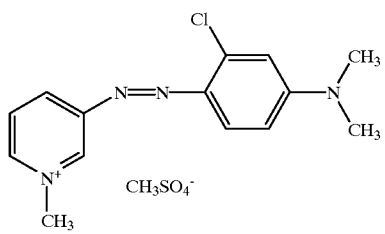
(IV)40
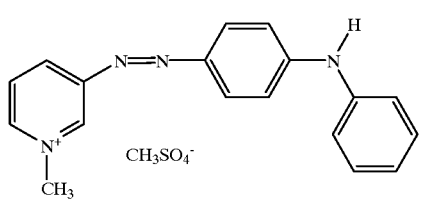
(IV)41
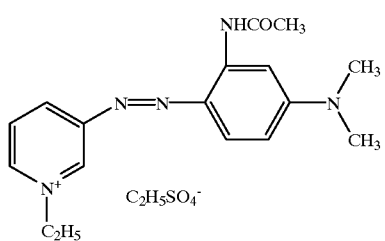
(IV)42
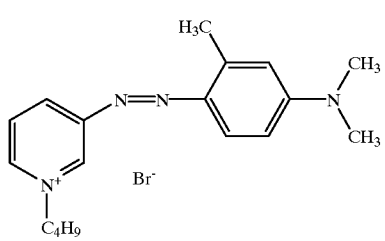
(IV)43
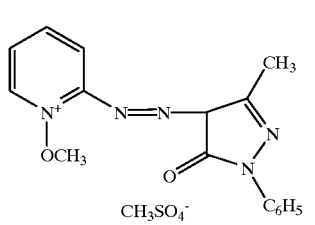
(IV)44
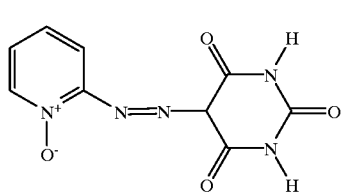
(IV)45
-continued
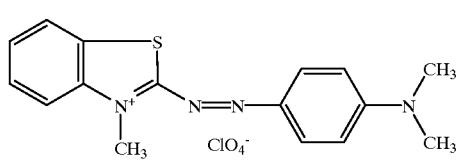
(IV)46
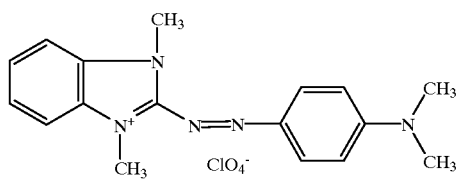
(IV)47
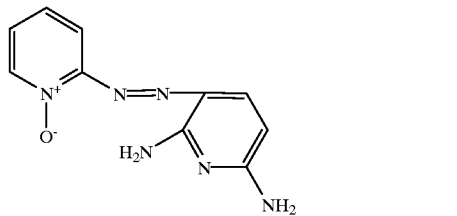
(IV)48
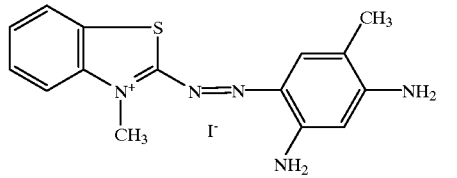
(IV)49
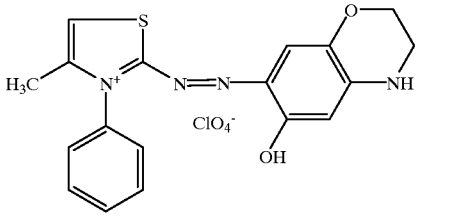
(IV)50
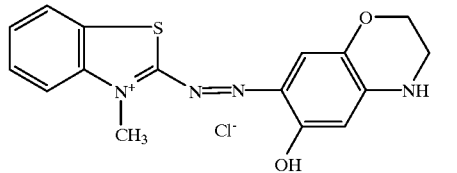
(IV)51
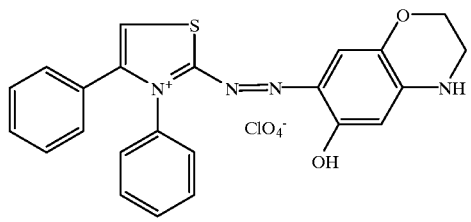
(IV)52

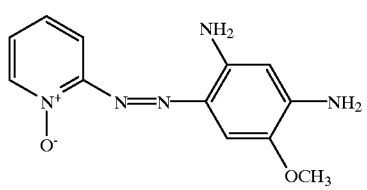
(IV)₅₃
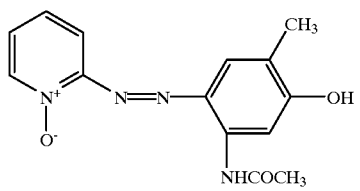
(IV)₅₄
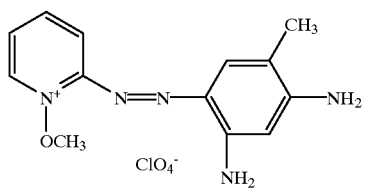
(IV)₅₅
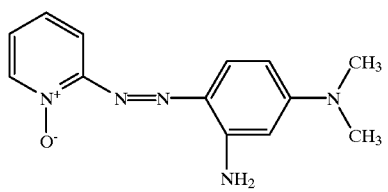
(IV)₅₆
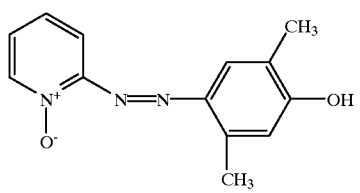
(IV)₅₇
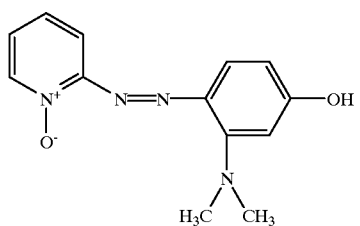
(IV)₅₈
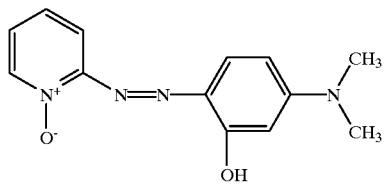
(IV)₅₉
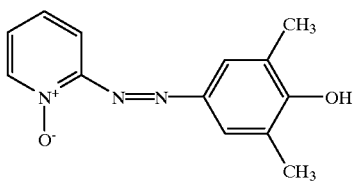
(IV)₆₀
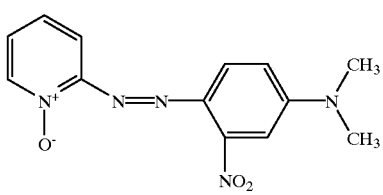
(IV)₆₁
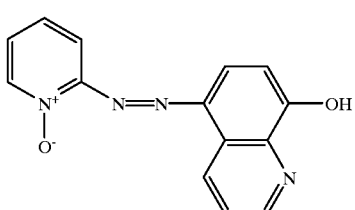
(IV)₆₂
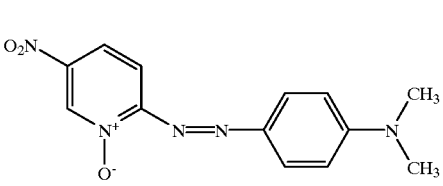
(IV)₆₃
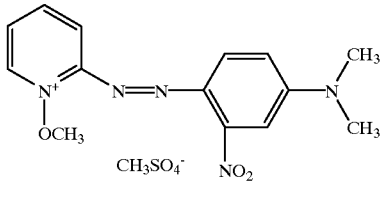
(IV)₆₄
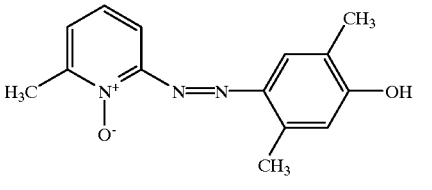
(IV)₆₅
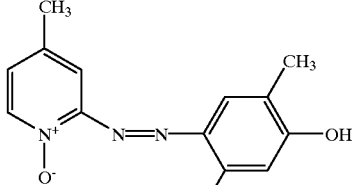
(IV)₆₆
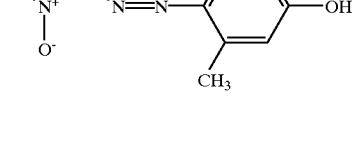

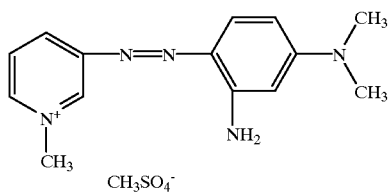
(IV)₆₇

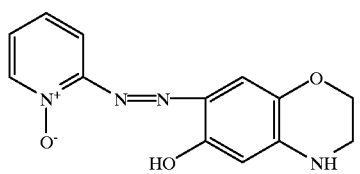
(IV)₆₈

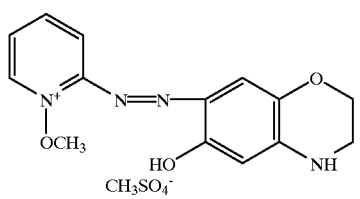
(IV)₆₉

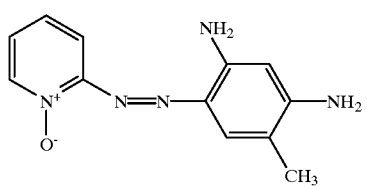
(IV)₇₀

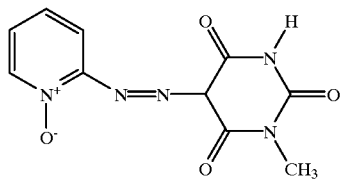
(IV)₇₁

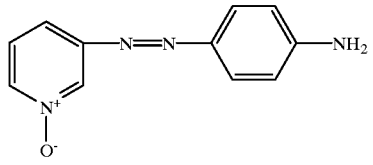
(IV)₇₂

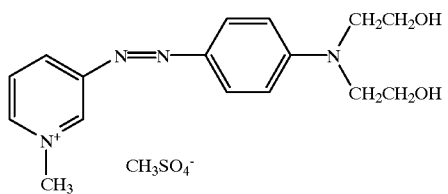
(IV)₇₃

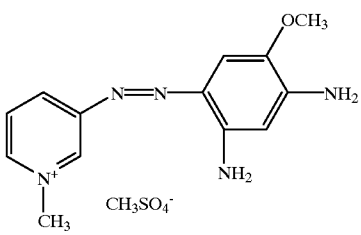
(IV)₇₄

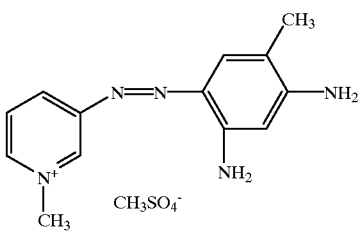
(IV)₇₅

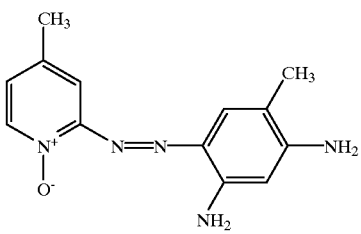
(IV)₇₆

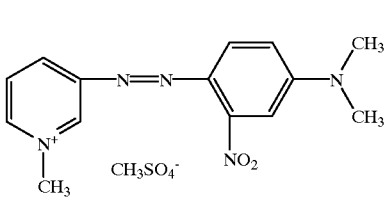
(IV)₇₇

The aqueous medium of the dye composition is made up solely of water or of a mixture of water and at least one cosmetic adjuvant chosen from the various adjuvants commonly used for dyeing keratin fibres, such as solvents, surfactants, polymers, inorganic or organic thickeners, antioxidants, penetrating agents, sequestering agents, fragrances, buffers, dispersing agents, conditioners, film-forming agents, ceramides, preserving agents and opacifiers.

According to the invention, the water preferably represents from 20 to 95% by weight relative to the total weight of the dye composition and even more preferably from 40 to 90% by weight relative to this weight.

According to the process of the invention, the dye composition can be ready to use or prepared at the time of use by mixing at least one pulverulent composition (P) containing at least one basic direct dye, and at least one aqueous composition (A).

The aqueous composition (A) can be water or a mixture of water and one or more cosmetic adjuvants such as those mentioned above.

In the pulverulent composition (P), the basic direct dye(s) can constitute, by itself(themselves), all of the pulverulent composition, or can be dispersed in an excipient, as powder, of organic nature and/or of inorganic nature. This powder preferably has a particle size of less than 350 μm.

The organic excipient can be of synthetic or plant origin and chosen in particular from crosslinked or non-crosslinked synthetic polymers, polysaccharides such as celluloses and modified or unmodified starches, as well as natural products containing them such as sawdust, or plant gums (guar gum, carob gum, xanthan gum, etc.).

The inorganic excipient can be metal oxides such as titanium oxides, aluminium oxides, kaolin, talc, silicates, mica and silicas.

An advantageously preferred excipient is sawdust such as Epicea sawdust.

The water-insoluble products which can constitute this inorganic or organic excipient can also be present in the dye composition as adsorption agent for the basic direct dye(s).

The pulverulent composition (P) can also contain binders or coating products in an amount preferably not exceeding 3% by weight approximately relative to the total weight of the said pulverulent composition.

These binders are preferably oils or liquid fats of mineral, synthetic, animal or plant origin.

The pulverulent composition can optionally also contain other adjuvants, in powder form, in particular surfactants of any nature and hair conditioners.

Needless to say, a person skilled in the art will take care to select the optional complementary compound(s) mentioned above, such that the advantageous properties intrinsically associated with the dye composition according to the invention, or with the pulverulent composition, are not, or are not substantially, adversely affected by the addition(s) envisaged.

According to the invention, the dye composition used during the second step of the process is applied to the keratin fibres for however long a dye-application time is necessary to obtain the colouring in the desired intensity, which is generally between 2 and 45 minutes and even more particularly between 3 and 10 minutes.

Concrete examples illustrating the invention will now be given without, however, being limiting in nature.

EXAMPLES

Examples 1 to 3

The various compositions below were prepared:

Oxidizing Composition: (common to Examples 1, 2 and 3)
  At the time of use, the following were mixed together:
  48 g of a powdered oxidizing composition containing:
  70% by weight of a mixture of sodium persulphate and potassium persulphate
  12% by weight of sodium metasilicate, and
  7% of ammonium chloride
  30 ml of a cream containing nonionic surfactants and 12 g of aqueous ammonia containing 20% $NH_3$
  and 30 ml of oxidizing milk having a pH of 2.0 and a hydrogen peroxide titre of 40 volumes (12% by weight).

Dye Compositions:
  At the time of use, the following were mixed together:
  60 g of an aqueous composition (A) containing:

| | |
|---|---|
| cetylstearyl alcohol | 7 g |
| ethanol | 2 g |
| coconut acid diethanolamide freed of the head fraction, sold under the name Comperlan KD by the company Henkel | 3 g |
| sodium cocoylamidoethylamine-N-hydroxyethyl-N-propionate | 6 g A.M.* |
| Preserving agents and fragrances | q.s. |
| demineralized water | 100 g |

*: A.M. = Active material 40 g of water, and
  3.5 g of a pulverulent composition (P) containing (contents in grams):

| Example | 1 | 2 | 3 |
|---|---|---|---|
| 1-(γ-Aminopropyl)aminoanthraquinone hydrochloride (basic direct dye) | 13 | — | — |
| Basic Red 76 (basic direct dye) | — | 45.7 | — |
| Basic Red 51 (basic direct dye) | — | — | 3 |
| Liquid petroleum jelly | 3 | 3 | 3 |
| Ground Epicea sawdust qs | 100 g | 100 g | 100 g |

The bleaching oxidizing composition was applied to three locks of dark chestnut hair for 40 minutes at room temperature. The locks of hair were bleached 6 tones, to a very light blonde.

After this first bleaching step, the locks of hair were rinsed, washed with shampoo, rinsed again and then dried.

Each of the dye compositions described above was then applied to each of the locks of hair thus bleached, for 5 minutes.

After rinsing and drying, the locks of hair were dyed in the shades featured in the table below:

| EXAMPLE | SHADE OBTAINED |
|---|---|
| 1 | Intense fuchsia |
| 2 | Intense coppery red |
| 3 | Intense fuchsia |

What is claimed is:

1. A process for the two-step direct dyeing of keratin fibres, comprising:
   a) bleaching the keratin fibres; and
   b) applying to the bleached keratin fibres a dye composition comprising at least one partially dissolved basic direct dye and an aqueous medium, wherein the partially dissolved basic direct dye is either in supersaturation or is partially or totally absorbed onto or coated with an insoluble inorganic or orqanic filler present in the dye composition,
   wherein the dye composition is ready to use or results from mixing, at the time of application, at least one pulverulent composition comprising at least one basic direct dye and an aqueous composition.

2. A process according to claim 1, wherein the keratin fibres are human hair.

3. A process according to claim 1, wherein the basic direct dye is in supersaturation.

4. A process according to claim 1, wherein the basic direct dye is partially or totally adsorbed onto or coated with an insoluble inorganic or organic filler present in the dye composition.

5. A process according to claim 1, wherein the bleaching step leads to a shade having a tone height of greater than or equal to about 6.

6. A process according to claim 1, wherein the bleaching step leads to a shade which shows a colour difference of greater than or equal to about 2 tones when compared with the colour of the fibres before bleaching.

7. A process according to claim 1, wherein the bleaching step is carried out by applying an oxidizing composition containing at least one oxidizing agent.

8. A process according to claim 7, wherein the oxidizing agent is hydrogen peroxide, urea peroxide, an alkali metal bromate, a persalt, or a polythionate, or a mixture thereof.

9. A process according to claim 7, wherein:
the oxidizing composition is in the form of a liquid or cream, and
the oxidizing composition is ready to use or results from mixing, at the time of use, at least one aqueous composition or at least one aqueous composition with at least one pulverulent composition, wherein the oxidizing agent is present in the aqueous composition or in the pulverulent composition, or in both.

10. A process according to claim 7, wherein the oxidizing composition has a pH of from about 5 to about 12.

11. A process according to claim 1, wherein the bleaching is carried out by irradiating the keratin fibres with laser light in the form of pulses which are powerful enough to degrade melanin contained in the keratin fibres.

12. A process according to claim 1, wherein the basic direct dye is a basic aminoanthraquinone dye, basic mono- or diazo dye, basic azomethine dye, basic naphthoquinone dye or an ethylenically monounsaturated basic dye.

13. A process according to claim 1, wherein the basic direct dye is chosen from:
(8-(p-aminophenyl)azo)-7-hydroxy-2-naphthyl) trimethylammonium chloride;
the combination of 3-(4-amino-6-bromo-5,8-dihydro-1-hydroxy-8-imino-5-oxo-2-naphthyl)amino)-N,N,N-trimethylbenzenaminium chloride and of 3-(2,6-dibromo-5,8-dihydro-1-hydroxy-8-imino-5-oxo-3-naphthyl)amino-N,N,N-trimethylbenzenaminium chloride;
7-hydroxy-8-((2-methoxyphenyl)azo)-N,N,N-trimethyl-2-naphthalenaminium chloride;
(8-((4-amino-2-nitrophenyl)azo)-7-hydroxy-2-naphthyl)-trimethylammonium chloride;
the combination of (8-((4-amino-3-nitrophenyl)azo-7-hydroxy-2-naphtyl)trimethylammonium chloride and of (8-((4-amino-2-nitrophenyl)azo)-7-hydroxy-2-naphthyl)trimethylammonium chloride;
3-(4,5-dihydro-3-methyl-5-oxo-1-phenyl-1H-pyrazol-4-yl)azo)-N,N,N-trimethyl-benzenaminium chloride; and
1-(γ-aminopropyl)aminoanthraquinone hydrochloride, 1-N-(methylmorpholiniumpropyl)-amino-4-hydroxyanthra-quinone methyl sulphate.

14. A process according to claim 1, wherein the basic direct dye is:

a) a compound of formula (I):

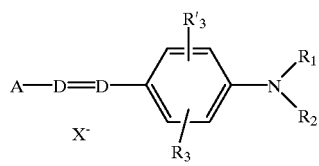

(I)

wherein:

D represents a nitrogen atom or a —CH group;

$R_1$ and $R_2$, which may be identical or different, represent a hydrogen atom; a $C_1$–$C_4$ alkyl radical which can be substituted with a —CN, —OH or —NH$_2$ radical or form, with a carbon atom of the benzene ring, a heterocycle optionally containing oxygen or an additional nitrogen or both, which can be substituted with one or more $C_1$–$C_4$ alkyl radicals; or a 4'-aminophenyl radical;

$R_3$ and $R'_3$, which may be identical or different, represent a hydrogen atom or a halogen atom, or a cyano, $C_1$–$C_4$ alkoxy or acetyloxy radical;

$X^-$ represents an anion; and

A represents:

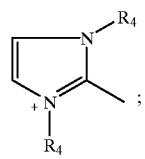

A$_1$

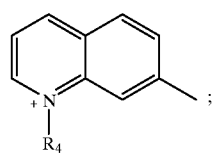

A$_2$

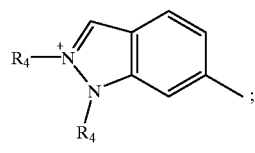

A$_3$

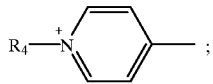

A$_4$

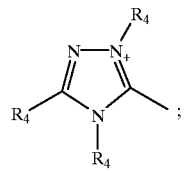

A$_5$

-continued

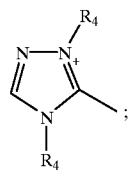  A6

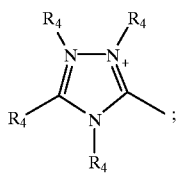  A7

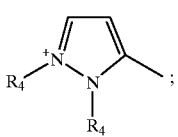  A8

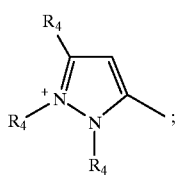  A9

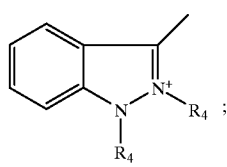  A10

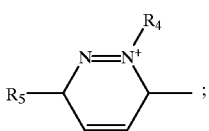  A11

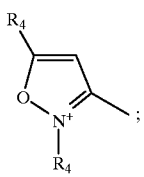  A12

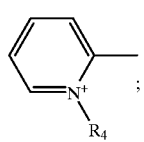  A13

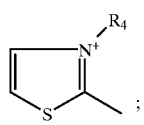  A14

-continued

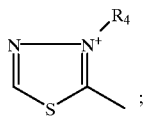  A15

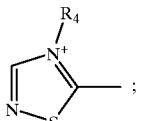  A16

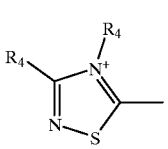  A17

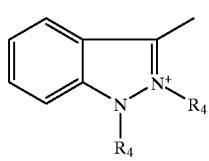  or  A18

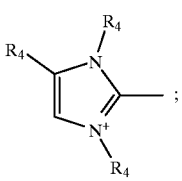  A19 wherein:
$R_4$ independently represents a $C_1$–$C_4$ alkyl radical, unsubstituted or substituted with a hydroxyl radical, and
$R_5$ represents a $C_1$–$C_4$ alkoxy radical,
with the proviso that when D represents —CH, A represents $A_4$ or $A_{13}$, and $R_3$ is other than an alkoxy radical, then $R_1$ and $R_2$ do not simultaneously denote a hydrogen atom;

b) a compound of formula (II):

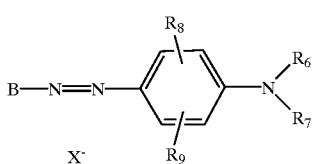

(II)

wherein:
$R_6$ represents a hydrogen atom or a $C_1$–$C_4$ alkyl radical;
$R_7$ represents a hydrogen atom, an alkyl radical which can be substituted with a —CN radical or with an amino group, or a 4′-aminophenyl radical, or forms with $R_6$ a heterocycle containing oxygen or an additional nitrogen or both, unsubstituted or substituted with a $C_1$–$C_4$ alkyl radical;
$R_8$ and $R_9$, which may be identical or different, represent a hydrogen atom, a halogen atom, a $C_1$–$C_4$ alkyl, $C_1$–$C_4$ alkoxy, or a —CN radical;

X⁻ represents an anion; and

B represents:

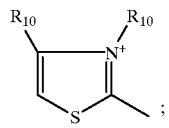  B1

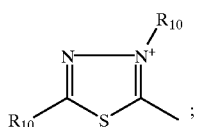  B2

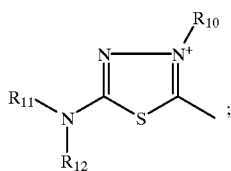  B3

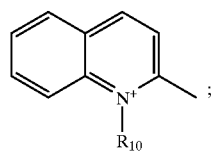  B4

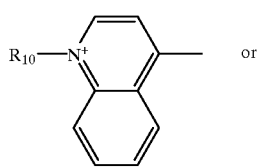  B5 or

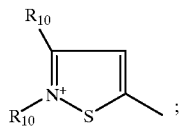  B6 wherein:

$R_{10}$ independently represents a $C_1$–$C_4$ alkyl radical, and $R_{11}$ and $R_{12}$, which may be identical or different, represent a hydrogen atom or a $C_1$–$C_4$ alkyl radical;

c) a compound of formulae (III) or (III'):

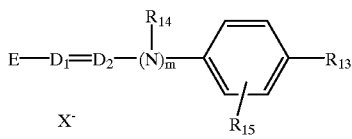  (III)

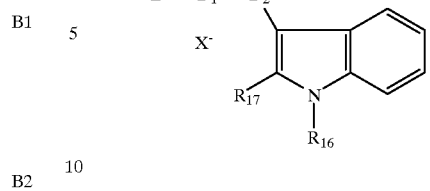  (III')

wherein:

$R_{13}$ represents a hydrogen atom, a $C_1$–$C_4$ alkoxy radical, a halogen atom or an amino radical;

$R_{14}$ represents a hydrogen atom, a $C_1$–$C_4$ alkyl radical or forms, with a carbon atom of the benzene ring, a heterocycle, wherein said heterocycle optionally contains oxygen, and is unsubstituted or substituted with one or more $C_1$–$C_4$ alkyl groups;

$R_{15}$ represents a hydrogen atom or a halogen atom;

$R_{16}$ and $R_{17}$, which may be identical or different, represent a hydrogen atom or a $C_1$–$C_4$ alkyl radical;

$D_1$ and $D_2$, which may be identical or different, represent a nitrogen atom or a —CH group;

m represents 0 or 1;

wherein when $R_{13}$ represents an unsubstituted amino group, then $D_1$ and $D_2$ simultaneously represent a —CH group and m=0;

X⁻ represents an anion; and

E represents a group chosen from the structures E1 to E8 below:

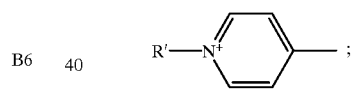  E1

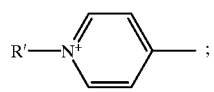  E2

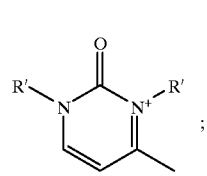  E3

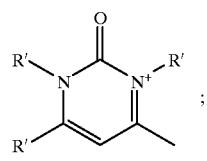  E4

E5

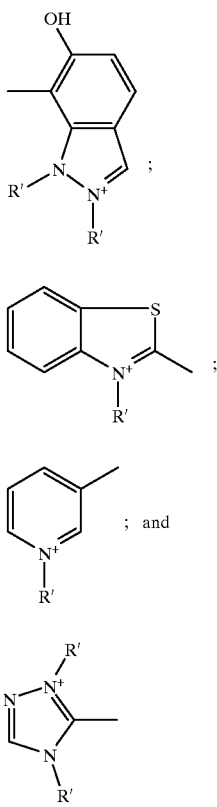

E6

E7

; and

E8 wherein R' represents a $C_1$–$C_4$ alkyl radical;
wherein when m=0 and $D_1$ represents a nitrogen atom, then E may also represent:

E9

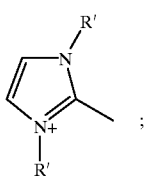

wherein R' represents a $C_1$–$C_4$ alkyl radical; or the basic direct dye is d) a compound of formula (IV):

$$G\text{—}N\text{=}N\text{—}J \quad (IV)$$

wherein:
G represents $G_1$, $G_2$ or $G_3$:

$G_1$

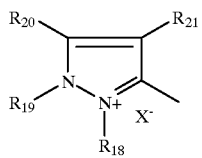

$G_2$

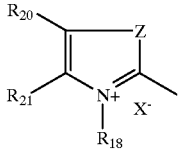

$G_3$

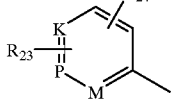

wherein:
$R_{18}$ denotes a $C_1$–$C_4$ alkyl radical, a phenyl radical, unsubstituted or substituted with a $C_1$–$C_4$ alkyl radical or a halogen atom;
$R_{19}$ denotes a $C_1$–$C_4$ alkyl radical or a phenyl radical;
$R_{20}$ and $R_{21}$, which may be identical or different, represent a $C_1$–$C_4$ alkyl radical, a phenyl radical, or
$R_{20}$ and $R_{21}$ together form, in $G_1$, a benzene ring substituted with one or more $C_1$–$C_4$ alkyl, $C_1$–$C_4$ alkoxy or $NO_2$ radicals, or
$R_{20}$ and $R_{21}$ together form, in $G_2$, a benzene ring unsubstituted or substituted with one or more $C_1$–$C_4$ alkyl, $C_1$–$C_4$ alkoxy or $NO_2$ radicals;
$R_{20}$ may also denote a hydrogen atom;
Z denotes an oxygen or sulphur atom or a group —$NR_{19}$;
M represents a —CH, —CR or —$NR_{22}(X^-)_r$ group, wherein R denotes $C_1$–$C_4$ alkyl and r denotes zero or 1;
K represents a —CH, —CR or —$NR_{22}(X^-)_r$ group, wherein R denotes $C_1$–$C_4$ alkyl and r denotes zero or 1;
P represents a —CH, —CR or —$NR_{22}(X^-)_r$ group, wherein R denotes $C_1$–$C_4$ alkyl and r denotes zero or 1;
$R_{22}$ represents an atom $O^-$, a $C_1$–$C_4$ alkoxy radical or a $C_1$–$C_4$ alkyl radical;
$R_{23}$ and $R_{24}$, which may be identical or different, represent a hydrogen atom, a halogen atom, a $C_1$–$C_4$ alkyl or $C_1$–$C_4$ alkoxy radical or an —$NO_2$ radical;
$X^-$ represents an anion;
with the provisos that,
at least one of K, P, or M denotes —$NR_{22}(X^-)_r$;
if $R_{22}$ denotes $O^-$, then r denotes zero;
if K or P or M denotes —N—($C_1$–$C_4$)alkyl $X^-$, then $R_{23}$ or $R_{24}$ is other than a hydrogen atom;
if K denotes —$NR_{22}(X^-)_r$, then M=P=—CH or —CR;
if M denotes —$NR_{22}(X^-)_r$, then K=P=—CH or —CR;
if P denotes —$NR_{22}(X^-)_r$, then K=M=—CH or —CR;
if Z denotes a sulphur atom with $R_{21}$ denoting $C_1$–$C_4$ alkyl, then $R_{20}$ is other than a hydrogen atom; and
if Z denotes —$NR_{22}$ with $R_{19}$ denoting $C_1$–$C_4$ alkyl, then at least one of the
radicals $R_{18}$, $R_{20}$ or $R_{21}$ of $G_2$ is other than a $C_1$–$C_4$ alkyl radical;

J represents:
(i) a group of structure $J_1$:

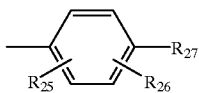

$J_1$ wherein:
- $R_{25}$ represents a hydrogen atom, a halogen atom, a $C_1$–$C_4$ alkyl or $C_1$–$C_4$ alkoxy radical, a radical —OH, —$NO_2$, —$NHR_{28}$, —$NR_{29}R_{30}$, or —$NHCO(C_1$–$C_4)$alkyl, or forms, with $R_{26}$, a 5- or 6-membered ring which may or may not contain one or more hetero atoms chosen from nitrogen, oxygen and sulphur;
- $R_{26}$ represents a hydrogen atom, a halogen atom, a $C_1$–$C_4$ alkyl or $C_1$–$C_4$ alkoxy radical, or forms, with $R_{27}$ or $R_{28}$, a 5- or 6-membered ring which may or may not contain one or more hetero atoms chosen from nitrogen, oxygen and sulphur;
- $R_{27}$ represents a hydrogen atom, an —OH radical, an —$NHR_{28}$ radical or an —$NR_{29}R_{30}$ radical;
- $R_{28}$ represents a hydrogen atom, a $C_1$–$C_4$ alkyl radical, a $C_1$–$C_4$ monohydroxyalkyl radical, a $C_2$—$C_4$ polyhydroxyalkyl radical or a phenyl radical;
- $R_{29}$ and $R_{30}$, which may be identical or different, represent a $C_1$–$C_4$ alkyl radical, a $C_1$–$C_4$ monohydroxyalkyl radical or a $C_2$—$C_4$ polyhydroxyalkyl radical;

(ii) a 5- or 6-membered heterocyclic group containing nitrogen, which can contain other hetero atoms or carbonyl groups and can be substituted with one or more $C_1$–$C_4$ alkyl, amino or phenyl radicals, or with a group of structure $J_2$:

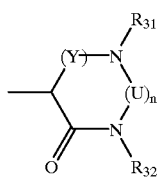

$J_2$ wherein:
- $R_{31}$ and $R_{32}$, which may be identical or different, represent a hydrogen atom, a $C_1$–$C_4$ alkyl radical or a phenyl radical;
- Y denotes a —CO— radical or a radical

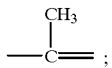

and
- n=0 or 1, wherein when n is 1, U denotes a —CO— radical.

15. A process according to claim 14, wherein the basic direct dye is a compound of formulae (I), (II), (III) or (III') and $X^-$ represents chloride, methyl sulphate or acetate ion.

16. A process according to claim 14, wherein the basic direct dye is a compound of formula (IV) and $X^-$ represents chloride, iodide, methyl sulphate, ethyl sulphate, acetate or perchlorate ion.

17. A process according to claim 14, wherein $R_3$, $R_{3'}$, $R_8$, $R_9$, $R_{13}$, $R_{15}$, $R_{18}$, $R_{23}$, $R_{24}$, $R_{25}$, and $R_{26}$ are each independently a chlorine, bromine, iodine or fluorine atom.

18. A process according to claim 1, wherein the aqueous medium of the dye composition comprises water or a mixture of water and at least one cosmetic adjuvant, wherein the cosmetic adjuvant is a solvent, surfactant, polymer, inorganic or organic thickener, antioxidant, penetrating agent, sequestering agent, fragrance, buffer, dispersing agent, conditioner, film-forming agent, ceramide, preserving agent or opacifier.

19. A process according to claim 18, wherein water represents from about 20 to about 95% by weight of the total weight of the dye composition.

20. A process according to claim 1, wherein, in the pulverulent composition, the basic direct dye constitutes all of the pulverulent composition, or is dispersed in an excipient, as powder, of organic nature or of inorganic nature.

21. A process according to claim 20, wherein the the basic direct dye is dispersed in an excipient which is sawdust.

22. A process according to claim 1, wherein the dye composition is applied for a dye-application time of from about 2 to about 45 minutes.

23. A process according to claim 1, wherein the composition is applied for a dye-application time of from about 3 to about 10 minutes.

* * * * *